United States Patent [19]
Huang et al.

[11] Patent Number: 5,940,468
[45] Date of Patent: Aug. 17, 1999

[54] CODED APERTURE X-RAY IMAGING SYSTEM

[75] Inventors: Suzhou Huang, Cambridge; Michael V. Hynes, Lincoln, both of Mass.

[73] Assignee: American Science and Engineering, Inc., Billerica, Mass.

[21] Appl. No.: 08/965,810

[22] Filed: Nov. 7, 1997

Related U.S. Application Data

[60] Provisional application No. 60/030,714, Nov. 8, 1996, and provisional application No. 60/034,792, Dec. 19, 1996.

[51] Int. Cl.⁶ .................................................. G01N 23/04
[52] U.S. Cl. .................................................. 378/57; 378/87
[58] Field of Search .................................. 378/57, 86, 87, 378/88, 89, 145, 149, 2

[56] References Cited

U.S. PATENT DOCUMENTS

| | | | |
|---|---|---|---|
| 4,209,780 | 6/1980 | Fenimore et al. | 340/146.3 |
| 4,423,522 | 12/1983 | Harding | 378/87 |
| 5,247,561 | 9/1993 | Kotowski | 378/87 |

FOREIGN PATENT DOCUMENTS

| | | |
|---|---|---|
| 0 061 547 A1 | 10/1982 | European Pat. Off. . |
| WO 92/02937 | 2/1992 | WIPO . |
| WO 97/45755 | 12/1997 | WIPO . |

*Primary Examiner*—David P. Porta
*Attorney, Agent, or Firm*—Bromberg & Sunstein LLP

[57] ABSTRACT

An X-ray imaging system which measures X-rays scattered by material concealed within an enveloping surface. A beam of X-ray radiation is incident on the enveloping surface and scattered onto one or more arrays of detectors. One or more masks of material opaque to X-ray transmission but for a series of apertures is interposed between the object and the detectors so as to cast shadows on different parts of the detector array. The image of the scattering material, as detected at the detector array, is modulated by the pattern of mask apertures. A controller reconstructs the image of the illuminated line. By scanning the illumination with respect to the object, an image of the entire object in scattered radiation is obtained, while use of multiple arrays or variation of geometrical settings allows reconstruction of the source of scattering in three dimensions.

20 Claims, 2 Drawing Sheets

CODED APERTURE X-RAY IMAGING SYSTEM

The present application claims priority from U.S. provisional application number 60/030,714, filed Nov. 8, 1996, and from U.S. provisional application number 60/034,792, filed Dec. 19, 1996, both of which provisional applications are herein incorporated by reference.

TECHNICAL FIELD OF THE INVENTION

The present invention relates to a system and method for reconstructing an image of a concealed object from X-ray radiation scattered by the concealed object. It is suited to detecting contraband, such as explosives, weapons or drugs which are concealed in an enveloping surface such as airline baggage or a shipping container.

BACKGROUND OF THE INVENTION

The use of scattered X-ray radiation for detection of concealed objects has been taught in many patents. It is well known that X-ray detectors may be placed at any position with respect to the object under scrutiny in order to capture photons scattered through the Compton process by the medium under scrutiny. The various placements of X-ray detectors around the object correspond to forward scatter, backscatter, and side scatter detectors, as the case may be. Since the number of X-ray photons scattered into a given solid angle is small, it is often desirable to capture scattered photons from a large solid angle in order to increase the sensitivity of the detection process. The use of large-area detectors, however, requires the implementation of stratagems in order to determine the precise origin, within the enveloping surface, of the detected photons, i.e., to spatially resolve the shape of the object under scrutiny even if it cannot be observed directly because it is contained within an enveloping surface.

One method of achieving spatial resolution has been to illuminate the object under scrutiny with a "pencil beam" or "flying spot" of X-ray radiation that is scanned with respect to the object in some sort of raster pattern. Obviously, motion of the object, as on a conveyor belt in one direction, is equivalent to a corresponding motion of the X-ray beam. Using this stratagem, only a particular position in a plane transverse to the propagation axis of the X-ray radiation is illuminated at a particular moment, so that an image of the entire scanned object can be reconstructed, but only after the scan is complete.

Using the raster-scanned flying-spot method, each position in the object is only illuminated for a small duration of time, since the entire area of the piece of luggage, for example, must be scanned as the luggage is conveyed on a conveyor belt across the path of the X-ray beam. Under these circumstances, sensitivity may be limited by noise since the system is typically "photon-starved." Spatial resolution is limited to the size of beam, at best, though actual resolution is typically worse due to the necessity of spatial averaging. It is, thus, desirable to gain a multiplex advantage by simultaneously illuminating a larger fraction of the object than would be illuminated by a beam corresponding roughly to the size of a spatial resolution element. To gain this advantage, it is necessary to implement another stratagem for reconstructing an image of the scattering source.

Additionally, implementation of a pencil beam method may entail the weight and mechanical complexity associated with the use of a chopper wheel for moving a heavy lead aperture in order to shape a high-energy x-ray beam.

SUMMARY OF THE INVENTION

In accordance with one aspect of the invention, in one of its embodiments, there is provided an imaging system for analyzing material. The imaging system has a source of penetrating radiation, the source emitting radiation in an illumination direction with respect to the object such as to illuminate a portion or the entirety of the object. Additionally, the imaging system has at least one array of segmented detectors, each array of segmented detectors having a detector axis, where each array of segmented detectors detects radiation scattered by the object and provides signals corresponding to the detected radiation. Finally, the imaging system has a mask with a plurality of apertures interposed between the object and each detector array. The source of penetrating radiation may be an X-ray source, and may be substantially monoenergetic.

In alternate embodiments of the invention, the source of penetrating radiation may emit a beam of radiation along a beam opening angle disposed with an orientation with respect to the illuminated object such as to illuminate a line on the object, and the detector axis or axes may have a vector component substantially parallel to the illuminated line. In a further alternative embodiment, the imaging system also has a scanning arrangement for moving the beam relative to the object in a direction having a component transverse to the orientation of the beam opening axis and a controller for reconstructing the image of the scattering object using the signals corresponding to the detected radiation.

In accordance with yet another embodiment of the present invention, the source of penetrating radiation emits pulses having a temporal feature of duration less than the time scale of propagation through the object and may further include an electronic circuit for resolving the distance between the source of scattered emission and the array of segmented detectors. The arrays of segmented detectors may also be energy-selective.

In accordance with a further aspect of the present invention, there is provided a method for analyzing concealed material within an enveloping surface, which method has the steps of illuminating a line on the enveloping surface with a beam of penetrating radiation having a beam opening axis disposed with an orientation with respect to the object, providing at least one detector array having an aperture mask interposed between the detector array and the enveloping surface such that radiation scattered by the material is incident onto the detector array through the aperture mask, measuring the radiation scattered by the material onto the detector array, reconstructing an image of the material scattering the radiation, and determining physical properties of the concealed material.

DETAILED DESCRIPTION OF SPECIFIC EMBODIMENTS

Figure 1:
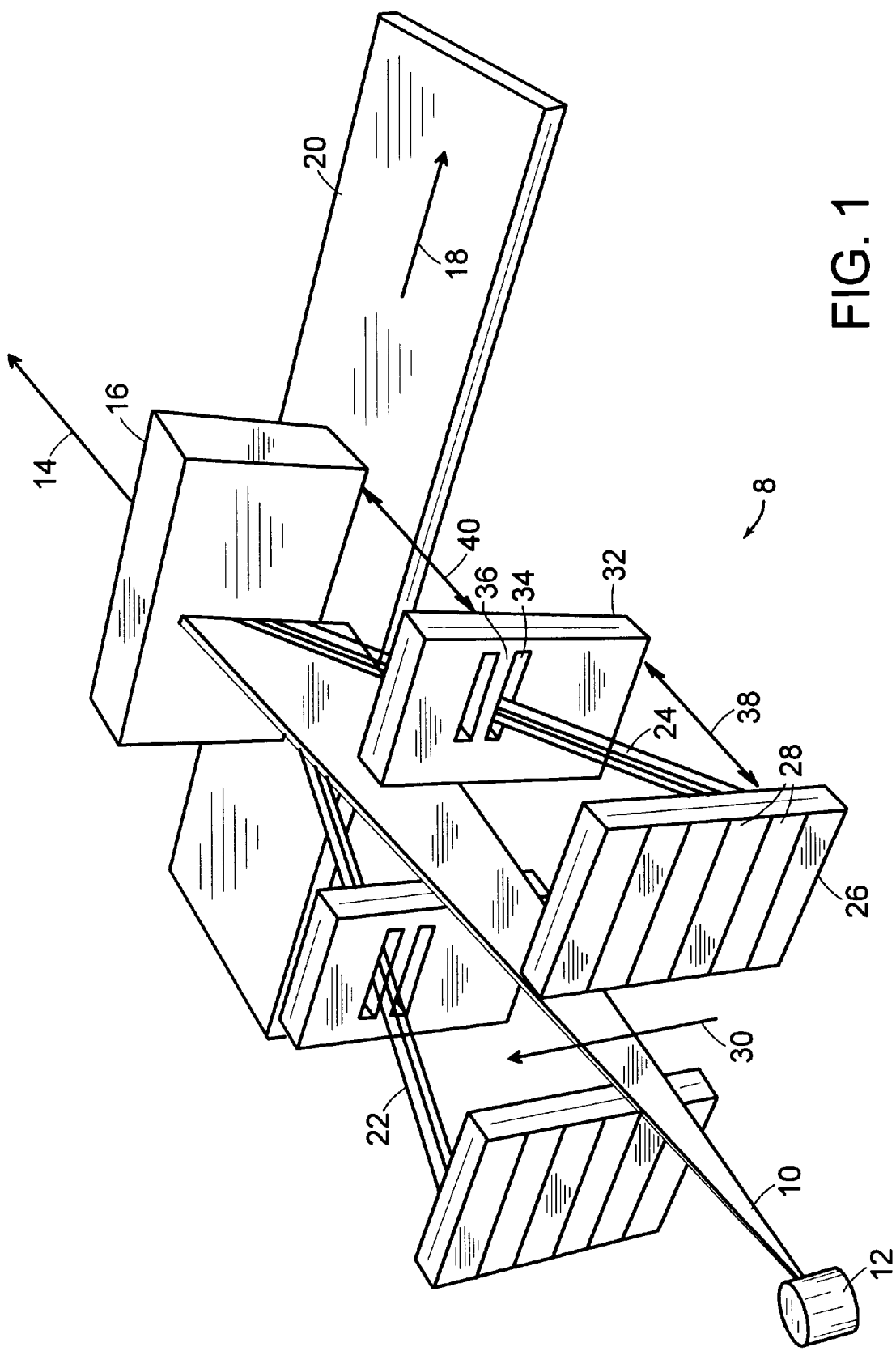
FIG. 1 is a diagram of a coded aperture system x-ray imaging system having segmented backscatter detector according to an embodiment of the invention.
Figure 2:
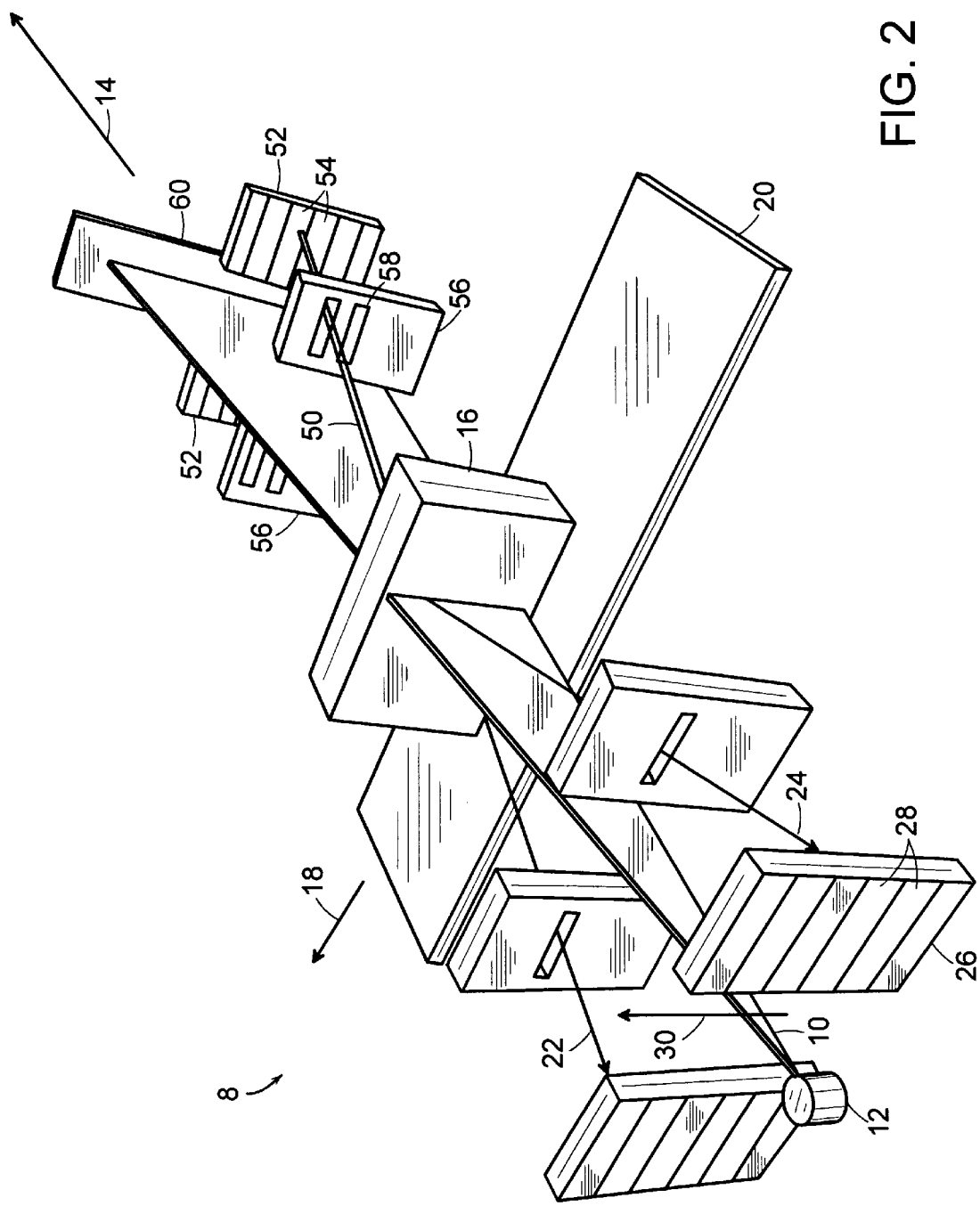
FIG. 2 is a diagram of a coded aperture x-ray imaging system having segmented backscatter, forward-scatter and transmission detectors according an alternate embodiment of the invention.

Referring to FIGS. 1 and 2, wherein like reference numerals designate identical or corresponding parts, and, more particularly, to FIG. 1, an X-ray imaging system is designated generally by numeral 8. X-ray beam 10 is emitted by an X-ray source 12 such as is known to persons skilled in the art. Beam 10 may also be comprised of other forms of penetrating radiation and may be monoenergetic, multienergetic, or, additionally, may change spectral characteristics in a temporal sequence. The temporal characteristics of X-ray source 12 and the X-ray beam 10 emitted thereby are discussed in further detail below. In a preferred embodiment of the invention, beam 10 is formed, using standard techniques, into a beam which is narrow in one dimension transverse to propagation axis 14 and fanned out in a second transverse dimension along axis 30, referred to as the beam opening axis. A beam shaped in this manner is referred to as a "fan beam." The present invention is advantageously applied in the case in which beam 10 is shaped as a fan beam, but may be applied, within the scope of this invention, to beams of other shapes.

X-ray beam 10 is configured to illuminate a pattern, which, in the case of a fan beam, is a line, on a side of a container 16. Container 16 may be any sort of enveloping surface which prevents the nature of its contents from being readily apparent and may include, for example, a suitcase or other sort of cargo, a car, truck, or other vehicle, an article of clothing, or a person or other subject. The orientation of container 16 is varied with respect to beams 10 so that beam 10 is incident upon container 16 at a variety of positions in temporal sequence. In the preferred embodiment, container 16 moves in horizontal direction 18 past beam 10 on a conveyor belt 20. Thus, in the course of the passage of container 16 past beam 10, the entirety of container 16 is illuminated by beam 10. There are alternative embodiments for providing coverage of a region of interest comprising a portion up to the entirety of a container and these include combinations of moving the container or scanning the beam, which, for purposes of this invention, are considered wholly equivalent. In particular, the beam of penetrating radiation may be scanned mechanically or electronically such as by scanning a cathode ray beam of x-ray source 12 with respect to the anode of the source.

Passage of beam 10 through container 16, or any other material object, gives rise to scattering of a portion of the X-ray energy in the beam incident on the object. Scattered X-ray energy is emitted through the Compton scattering process into all directions. Rays 22 and 24 are shown as examples of directions in which scattered X-ray radiation is re-emitted by the illuminated object.

In accordance with a preferred embodiment of the invention, one or more segmented detector arrays 26 of X-ray detectors 28 is positioned so as to receive X-ray energy scattered from container 16. It is to be understood that the precise placement of detector arrays 26 is purely a matter of design choice, since, as stated, scattered X-rays are emitted by container 16 in all directions. The X-ray detector segments 28 are arrayed within each detector array 26 in a direction having a vector component parallel to axis 30 of the long dimension of beam 10. Detector segments 28 may be extended in the direction transverse to axis 30 in order to intercept scattered X-ray energy with greater efficiency. In the direction of axis 30, however, the width over which detector segments 28 are sensitive is limited by collimators, or otherwise, so as to provide optimal spatial resolution.

Aperture masks 32 are located in the lines-of-sight between each detector array 26 and container 16 such that scattered X-ray radiation along ray 24 may reach detector array 26 only by traversing aperture mask 32. Aperture mask 32 contains a linear pattern of open segments or apertures 34 and closed segments 36. Apertures 34 and closed segments 36 allow, X-ray radiation to pass and block X-ray radiation, respectively. Aperture masks 32 thus cast X-ray shadows, in a determined pattern, on detector arrays 26. Since the detection pattern is one-dimensional, the pattern of apertures 34 of aperture masks 32 is realized as a pattern of slits. The pattern of apertures may be quasi-random or may be designed to optimize resolution of objects of a desired range of sizes, according to methods known to persons skilled in the art of super-resolved imaging, as is applied, for example, in astrophysical optics. If used, exclusively, with back-scattered radiation, the material out of which aperture masks 32 are constructed may be thin sheets of lead or tungsten, for example, since back-scatter photons are limited, physically, to half the rest-mass of an electron (255 keV), no matter how energetic the incident X-ray beam 10.

The use of aperture masks to image the contents of container 16 is described as follows. The material within container 16 which is illuminated by fan beam 10 emits scattered radiation which may be characterized as a linear array s. The shape of the object or objects emitting scattered radiation cannot be determined from the scattered radiation alone, since an entire line of container 16 is illuminated, and since every illuminated point scatters X-rays in all directions. However, scattered radiation 24 passes through aperture mask 32, which casts a different shadow on detector array 26 depending on the position within container 16 from which the scattered emission originates. The linear distribution of X-ray radiation detected by detector array 26 can be represented as a linear array d. The optical effect of passage of radiation through aperture mask 32 can be represented by aperture matrix A which relates s and detected scattered radiation d according to d=As. Since scattered radiation d at detector array 26 has passed through aperture mask 32, it is a matter of algorithmic manipulation to reconstruct an image of container 16 in to backscattered X-ray radiation by finding the pseudo-inverse of aperture matrix A and applying it to the detected signal vector d. Decomposition methods for inverting A are known in the art and may be found in mathematics texts such as Golub & Van Loan, *Matrix Computations* (Baltimore: JHU), which is hereby incorporated by reference.

Reconstruction of the image of container 16 in scattered radiation entails a computation of the pseudo-inverse of aperture matrix A which, in turn, embodies information regarding the pattern of apertures 34 and the respective distances 38 and 40 between detector array 26 and aperture mask 32 and between aperture mask 32 and the source of scattered X-rays within container 16. The requisite information is derived either calculationally or on the basis of a calibration procedure, as is known to persons skilled in the art. Since the object 16 being imaged in scattered radiation is comparable in size with the backscatter detector 26, both the scattering source and aperture mask 32 are effectively in the near-field of the detector, contrary to the case, such as where coded apertures are applied in astrophysics, in which the source is effectively at optical infinity and the incident rays of light are effectively parallel. Additionally, the matrix obtained is typically ill-conditioned and not amenable to standard inversion techniques. Consequently, standard reconstruction algorithms cannot be applied. In a preferred embodiment of the invention, singular value decomposition (SVD) of aperture matrix A is used, in a manner which can be proven to be optimal in reducing the mean-square deviation given the noise environment of the detection process and the finite duration of time allowed, for example, in baggage handling applications.

In a preferred embodiment of the invention, for imaging objects on the order of 1 meter in size, the number N of aperture elements is typically 256 or 512. The use of SVD in image processing, given full illumination of an object, would require immense resources in both CPU and memory. Construction of an image line by tine, as described above in reference to fan-beam illumination, has the advantage of significantly reducing the computational demands of the algorithm. In particular, once aperture matrix A has been inverted, through use of the SVD algorithm or otherwise, the computation required in order to reconstruct the desired image scales as $N^3$ in required CPU and $N^2$ in memory, since the inverted matrix, resident in memory, is to be multiplied by detected signal vector d. A comparable algorithm applied to the entire two-dimensional image would scale as $N^4$ is both CPU and memory. Once the aperture matrix A has been inverted for a given aperture mask 36 and relative placement of object 16, mask 36, and detector array 26, the pseudo-inverse matrix may then be stored and used for all subsequent computations, so that only multiplications need be performed in real time.

Image reconstruction from the detected signal vector d, using standard techniques, applies in a straightforward manner to radiation backscattered with angular uniformity via the Compton process. Indeed, the Compton scattering cross section is very flat at backward directions, typically within a 30° cone of the illumination axis in the backward direction. Persons skilled in the art will recognize that the angular distribution of scattering in the forward direction is a function of the energy of the scattered X-rays. Thus, additional steps, as discussed below, are required to deconvolve the scattering profile. Referring now to FIG. 2, the X-ray imaging system, designated generally by numeral 8 is shown, as in FIG. 1, with the addition of ray 50, shown to represent a typical direction of forward scattering. At side and forward scattering directions, the non-uniform angular distribution of the Compton scattering exhibits an increasing dependence on the energy of the scattered X-ray photon, particularly when the energy of the incoming photon is comparable with or greater than the rest mass of an electron ($\geq 500$ KeV).

In the forward scattering case depicted with respect to ray 50 in FIG. 2, one or more segmented detector arrays 52 of X-ray detectors 54 is positioned to receive X-ray energy forward scattered from container 16. The X-ray detector segments 54 are arrayed within each detector array 52 in a direction having a vector component parallel to ax'is 30 of the long dimension of beam 10. Aperture masks 56 contain linear patterns of open segments or apertures 58 in the manner of aperture masks 32 described above with reference to back-scatter. Aperture masks 56 thus cast X-ray shadows, in a determined pattern, on detector arrays 52. Additionally, a segmented X-ray detector array 60 may be positioned in the direct path of X-ray beam 10 to receive the portion of the X-ray illumination following attenuation by objects within the path of the beam through container 16. Attenuation data may further complement scatter imaging in the detection of threat materials, in manners known to persons skilled in the art.

Due to the aforesaid dependence of the angular distribution of Compton scattering in the forward direction on photon energy, aperture matrix A will have an energy dependence. In order to apply the deconvolution process described above to reconstruct an image of container 16 from X-ray energy forward-scattered through aperture masks 56, the energy dependence of A must be removed, either through system design or algorithmically. In a preferred embodiment, object 16 is illuminated with a nearly monoenergetic X-ray beam 10. In this case, aperture matrix A may be corrected by using the known Compton scattering cross section as a function of angle at the given incident energy, the so-called Klein-Nishina relation, known to persons skilled in the art. Alternative decomposition algorithms include, for example, the use of multiple X-ray beam energies in time sequence, including an energy chirp, or the placement of aperture masks 54 and associated detector arrays 52 at a plurality of distinct azimuthal angles with respect to incident X-ray beam 10.

In addition to the use of Compton-scatted photons for image reconstruction, X-ray imaging system may be used to image object 16 in X-ray photons at 0.5 MeV created due to the annihilation of slowed positrons. An incident X-ray beam 10 of energy exceeding 1 MeV will create electron-positron pairs giving rise to the resonant signal. A detector array 26 in the backward direction designed, as known to persons skilled in the art, to discriminate against photons at energies substantially different from 0.5 MeV will provide a low-background signal-to-noise advantage. Similarly, detector array 26 -nay employ energy selectivity to select for fluorescence or other resonant processes. Thus, the presence of particular atoms may be detected on the basis of X-ray spectroscopic signatures.

Once an image of the scattered radiation is available through application of the teachings above, it is then possible, using techniques known to persons skilled in the art of X-ray threat analysis, to combine the scattering image and the results of other measurements to determine not only the shape but also the density and atomic r umber of the concealed contents of container 16. For example, irradiation of container 16 with beam 10 permits simultaneous acquisition of an image of X-ray transmission through container 16, using a linear array of detectors aligned with the fan beam.

An additional application of the present invention is to X-ray tomography. Since aperture matrix A is a function of the relative placement of object 16 and detector array 26, the depth of the scattering source along the propagation direction 14 of the X-ray beam 10 may be solved for as part of the algorithm, thereby deriving a three-dimensional image of the scatterer. Aperture matrix A is sharply in focus for only one geometrical configuration of scatterer with respect to aperture mask 32 and detector array 26. Use of the pseudo-inverse of aperture matrix A sharply decodes the signal corresponding to only this particular geometrical configuration and blurs other signals which are out-of-focus. Since the backscatter signal decays quickly with increasing distance, decoding may be performed, for example, using an iterative method. First, the closest layer is reconstructed and removed from the detected signal. Then the second layer is decoded, followed, seriatim, by successive layers.

The limited contrast resolution provided by the foregoing method may be overcome by application of another embodiment of the invention based on the recognition that the detected signal is a sum over signals derived from a continuum of individual layers. In accordance with this embodiment, either multiple scans are made of the same object using a plurality of geometrical settings or else multiple detector arrays are disposed at differing positions with respect to the object, with an aperture mask corresponding to one or more of the detector arrays. Variation of the geometrical setting may be achieved, for example, by moving the relative placement of the coded aperture with respect to the corresponding detector array, or, alternatively, by moving the scanned object with respect to the coded aperture. Additionally, a combination of multiple geometrical settings and multiple coded apertures may be employed. The signals derived from the multiplicity of detector arrays and geometrical settings are assembled to constitute a super aperture matrix. Each diagonal block of the super aperture matrix corresponds to an aperture matrix of a single scan, in the case of multiple geometrical settings, or to one of the detector arrays, in the multiple detector arrangement. The super aperture array formed in the manner described operates directly on the (three-dimensional) space of the pixel real position and depth within the object. The SVD method is applied to obtain the pseudo-inverse of the super aperture matrix, thereby providing a solution for each layer within the object. Mixing of blurred signals from other layers may be avoided in this manner.

In yet a further alternate embodiment, a pulsed X-ray source 12 is employed to provide a pulsed X-ray beam 10 having a pulse duration, or a temporal feature, which is short on the time scale of propagation of the X-ray beam 10 through object 16. The precise distance traveled by the scattered X-ray photon to detector segment 28 is determined by electronic circuits, including gated amplifiers, known to persons skilled in the art. This provides true tomographic capability to imaging system 8.

It will be recognized by persons skilled in the art of X-ray imaging that the invention described herein permits the more efficient use of X-ray energy than in previous scatter imaging methods, thereby improving photon statistics and increasing signal-to-noise and sensitivity while reducing power consumption requirements. It will also be recognized that the method and apparatus taught in the present application may be used for areal or tomographic imaging of the body or of organs within the body.

The described embodiments of the invention are intended to be merely exemplary and numerous variations and modifications will be apparent to those skilled in the art. All such variations and modifications are intended to be within the scope of the present invention as defined in the appended claims.

We claim:

1. An imaging system for analyzing material, comprising:
   a. a source of penetrating radiation emitting radiation in a direction with respect to an object such as to illuminate a portion of the object up to the entirety thereof;
   b. at least one array of segmented detectors, each array of segmented detectors having a detector axis, for detecting radiation scattered by the object and providing a vector of signals corresponding to the detected radiation;
   c. a mask having a plurality of apertures interposed between the object and the detector array in such a manner that each segmented detector detects radiation scattered through more than one aperture; and
   d. a controller for applying to the vector of signals an operator corresponding to the plurality of apertures in such a manner as to derive an image corresponding to the object.

2. A system according to claim 1, wherein the source of penetrating radiation is an X-ray source.

3. A system according to claim 1, wherein the source of penetrating radiation is a substantially monoenergetic X-ray source.

4. A system according to claim 1, wherein the source of penetrating radiation emits a beam of radiation along a beam opening axis disposed with an orientation with respect to the object such as to illuminate a line on the object.

5. A system according to claim 4, wherein the at least one detector axis has a vector component substantially parallel to the illuminated line.

6. A system according to claim 4, further including a scanning arrangement for moving the beam relative to the object in a direction having a component transverse to the orientation of the beam opening axis.

7. A system according to claim 6, wherein the scanning arrangement includes a swept cathode ray incident upon a stationary anode.

8. A system according to claim 4, further including a conveyance mechanism for moving the object relative to the beam in a direction having a component transverse to the orientation of the beam opening axis.

9. A system according to claim 1, further including a controller for reconstructing the image of the object using the signals corresponding to the detected radiation.

10. A system according to claim 1, wherein the source of penetrating radiation emits pulses having a duration less than the time scale of propagation through the object.

11. A system according to claim 10, further including an electronic circuit for resolving the distance between the source of scattered emission and the at least one array of segmented detectors.

12. A system according to claim 1, wherein the at least one array of segmented detectors is energy-selective.

13. A method for analyzing concealed material within an enveloping surface, comprising:
   a. providing at least one array of detectors having an aperture mask interposed between the array and the enveloping surface such that radiation scattered by the material is incident onto each detector through more than one aperture of the aperture mask;
   b. measuring the radiation scattered by the material onto the array for creating a vector of signals corresponding to the detected radiation;
   c. applying an operator to the vector in such a manner as to reconstruct an image of the material scattering the radiation; and
   d. determining physical properties of the concealed material using the radiation scattered by the material and the image of the material.

14. A system according to claim 1, further comprising a plurality of arrays of segmented detectors such that at least one of the plurality of arrays is at a distance from the object different from the distance between the object and any other of the plurality of arrays of segmented detectors.

15. A system according to claim 1, wherein the mask may be moved with respect to the object.

16. A system according to claim 1, wherein the mask may be moved with respect to the at least one array of segmented detectors.

17. A method for deriving a tomographic image of an object, the method comprising:
   a. illuminating the object with penetrating radiation;
   b. providing at least one detector array having a plurality of detectors having an aperture mask interposed between the detector array and the object such as to form a first geometrical configuration of the detector array, aperture mask and object, and further such that radiation scattered by the object is incident onto the detector array through the aperture mask in such a manner that each detector detects radiation scattered through more than one aperture;
   c. measuring the radiation scattered by the object onto the detector array;
   d. reconstructing a first image of the object scattering the radiation;
   e. modifying a position of at least one of the object, the detector array, and the aperture mask such as to form a second geometrical configuration different from the first geometrical configuration;

f. remeasuring the radiation scattered by the object onto the detector array;

g. reconstructing a second image of the object scattering the radiation; and h. comparing the first and second images so as to derive a depth component of the object.

18. A method according to claim 17, further including the step of storing successive measurements of scattered radiation at a plurality of geometrical configurations in a super aperture matrix.

19. A method according to claim 18, further including the step of inverting the super aperture matrix for providing a solution for each of a plurality of layers within the object.

20. An imaging system for analyzing material, comprising:

a. a source of penetrating radiation emitting radiation having an energy distribution in a direction with respect to an object such as to illuminate a portion of the object up to the entirety thereof;

b. at least one array of segmented detectors, each array of segmented detectors having a detector axis, for detecting in a manner substantially independent of the energy distribution radiation scattered by the object and providing signals corresponding to the detected scattered radiation; and c. a mask having a plurality of apertures interposed between the object and the detector array in such a manner that each segmented detector detects radiation scattered through more than one aperture; and d. a controller for applying to the signals an operator corresponding to the plurality of apertures in such a manner as to derive an image corresponding to the object.

* * * * *